United States Patent [19]

Tyers

[11] Patent Number: 5,204,356
[45] Date of Patent: Apr. 20, 1993

[54] TREATMENT OF ANXIETY

[75] Inventor: Michael B. Tyers, Welwyn, England

[73] Assignee: Glaxo Group Limited, London, England

[21] Appl. No.: 827,511

[22] Filed: Jan. 29, 1992

Related U.S. Application Data

[60] Continuation of Ser. No. 530,301, May 30, 1990, abandoned, which is a division of Ser. No. 419,728, Oct. 11, 1989, Pat. No. 4,975,436, which is a division of Ser. No. 259,719, Oct. 19, 1988, Pat. No. 4,883,803, which is a continuation of Ser. No. 888,467, Jul. 23, 1986, abandoned.

[30] Foreign Application Priority Data

Jul. 24, 1985 [GB] United Kingdom ............. 8518658

[51] Int. Cl.$^5$ ................. A61K 31/44; A61K 31/415
[52] U.S. Cl. ............................. 514/304; 514/282; 514/305; 514/397
[58] Field of Search ............... 514/304, 305, 397, 282

[56] References Cited

U.S. PATENT DOCUMENTS

| | | | |
|---|---|---|---|
| 4,695,578 | 9/1987 | Coates et al. | 514/397 |
| 4,721,720 | 1/1988 | Wootton et al. | 514/304 |
| 4,725,603 | 2/1988 | Sanger et al. | |
| 4,725,615 | 2/1988 | Coates et al. | 514/397 |
| 4,749,718 | 6/1988 | Coates et al. | 514/397 |
| 4,783,478 | 11/1988 | Wootton et al. | |
| 4,786,643 | 11/1988 | Sanger et al. | |
| 4,808,581 | 2/1989 | Oxford et al. | 514/312 |
| 4,851,407 | 7/1989 | Wootton et al. | |
| 4,886,808 | 12/1989 | King. | |

FOREIGN PATENT DOCUMENTS

| | | |
|---|---|---|
| 094742 | 11/1983 | European Pat. Off. . |
| 099194 | 1/1984 | European Pat. Off. . |
| 158265 | 10/1985 | European Pat. Off. . |
| 300423 | 1/1986 | European Pat. Off. . |
| 191562 | 8/1986 | European Pat. Off. . |
| 200444 | 11/1986 | European Pat. Off. . |
| 201165 | 11/1986 | European Pat. Off. . |
| 214772 | 3/1987 | European Pat. Off. . |
| 221702 | 5/1987 | European Pat. Off. . |
| 230718 | 8/1987 | European Pat. Off. . |
| 235878 | 9/1987 | European Pat. Off. . |
| 247266 | 12/1987 | European Pat. Off. . |
| 2100259 | 12/1982 | United Kingdom . |
| 2125398 | 3/1984 | United Kingdom . |
| 2153821 | 8/1985 | United Kingdom . |

OTHER PUBLICATIONS

Stein et al., *Adv. Biochemical Psychopharmacology*, 14, 29–44, 1975.

Iversen, "5-HT and Anxiety," *Neuropharm.*, 1984, 23, 1553–1560.

*Primary Examiner*—S. J. Friedman
*Attorney, Agent, or Firm*—Bacon & Thomas

[57] ABSTRACT

The invention relates to the use of compounds which act as 5-hydroxytryptamine (5-HT) antagonists at 5-HT "M" receptors in the treatment of anxiety.

5 Claims, No Drawings

TREATMENT OF ANXIETY

This application is a continuation of application Ser. No. 07/530,301, filed May 30, 1990, now abandoned, which is a divisional of application Ser. No. 07/419,728, filed Oct. 11, 1989, now U.S. Pat. No. 4,975,436, which is a divisional of application Ser. No. 07/259,719, filed Oct. 19, 1988, now U.S. Pat. No. 4,883,803, which is a continuation of application Ser. No. 06/888,467, filed Jul. 23, 1986, now abandoned.

This invention relates to a new medical use for certain chemical compounds and pharmaceutical compositions containing them. In particular it relates to the use in the treatment of anxiety of compounds which act as antagonists of 5-hydroxytryptamine (5-HT) at receptors known in the art as 5-HT 'M' or 'M-like' receptors. Such receptors have been described for example by Fozard et al., Eur. J. Pharmacol., 59 (1979), 195–210; Ireland, Straughan and Tyers, Br. J. Pharmacol., 75, (1982) 16P; Humphrey, Neuropharmacology, 23 (1984) 1503–1570; and Richardson et al., Nature, 316, 126–131, 1985. For convenience, we will refer to them in this specification as 5-HT 'M' receptors.

5-HT receptors of this type are located for example on the terminals of afferent sensory neurones. Compounds which act as antagonists of 5-HT at 5-HT 'M' receptors may be identified using standard tests, for example, in vitro by measuring their inhibition of the depolarising effect of 5-HT on the rat or rabbit isolated vagus nerve or the rabbit isolated heart, or in vivo by measuring their effect on the Von Bezold-Jarisch reflex (induced by 5-HT) as described for example in the above-mentioned references.

A variety of compounds which act as antagonists of 5-HT at 5-HT 'M' receptors have been described in the art. The known compounds are generally azabicyclo derivatives and/or benzoic acid derivatives. Azabicyclo derivatives include compounds containing a bridged piperidyl group, such as a tropyl, pseudotropyl, homotropyl or quinuclidinyl group. An azabicyclo derivative preferably contains a carbocyclic or heterocyclic aromatic group conjugated, for example as an ester or amide, with the azabicyclic ring. The aromatic group may be for example an optionally substituted phenyl, indolyl, benzofuranyl, benzothienyl or pyrimidinyl group.

Benzoic acid derivatives which act as antagonists of 5-HT at 5-HT 'M' receptors include benzoates and benzamides. A benzoic acid derivative may for example be an ester or an amide formed with an azabicyclic group as defined above, or formed with a piperidyl group.

Such compounds have been disclosed inter alia in published UK Patent Applications Nos. 2100259, 2125398, 2131420, 2132189 and 2145416 and published European Patent Applications 111608, 116255 and 158265. The compounds disclosed in published European Patent Application 94742 are also antagonists of 5-HT at 5-HT 'M' receptors.

The compounds disclosed in these specifications have been described as being of use in a variety of conditions, including migraine. However there is no disclosure in these specifications of compounds which are antagonists of 5-HT at 5-HT 'M' receptors being of use in the treatment of anxiety.

Anxiety is widely treated by administering benzodiazepines such as diazepam, chlordiazepoxide or lorazepam. However the benzodiazepines are known to cause a number of serious side effects including dependence and drowsiness.

We have now found that compounds which act as 5-HT antagonists at 5-HT 'M' receptors are of use in the treatment of anxiety.

It should be understood that references in this specification to treatment include prophylactic treatment as well as the alleviation of symptoms.

Our UK Patent Application No. 2153821A and European Patent Application No 86300423 disclose tetrahydrocarbazolone derivatives which are potent and selective antagonists of 5-HT-induced responses in the rat isolated vagus nerve preparation. They can thus be identified as antagonists of 5-HT at 5-HT 'M' receptors. These tetrahydrocarbazolone derivatives have the general formula (I)

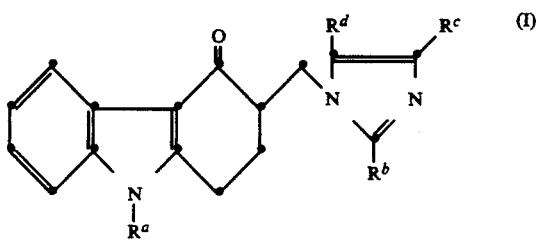

wherein $R^a$ represents a hydrogen atom or a $C_{1-10}$ alkyl, $C_{3-7}$ cycloalkyl, $C_{3-7}$cycloalkyl-($C_{1-4}$)alkyl, $C_{3-6}$ alkenyl, $C_{3-10}$ alkynyl, phenyl or phenyl-($C_{1-3}$)alkyl group, and one of the groups represented by $R^b$, $R^c$ and $R^d$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; and physiologically acceptable salts and solvates, e.g. hydrates, thereof.

It is stated in UK Specification No. 2153821A and European Patent Application 86300423 that the compounds of formula (I) may be useful inter alia for treating anxiety. The compounds of formula (I) as defined above are therefore excluded from the presently claimed invention. The compounds of formula (I) as defined above are also described and claimed in copending U.S. application Ser. No. 820,743, filed Jan. 22, 1986, which also describes their use, inter alia, for treating anxiety. The entire disclosure of U.S. application Ser. No. 820,743, filed Jan. 22, 1986, is herein incorporated by reference. The compounds of formula (I) as defined above are therefore excluded from the presently claimed invention, as is the method of treating anxiety using these compounds which is included in the copending application.

According to one aspect of the invention, therefore, we provide a method of treatment of a human or animal subject suffering from or susceptible to anxiety which comprises administering an effective amount of a compound which acts as an antagonist of 5-HT at 5-HT 'M' receptors (excluding compounds of formula (I) as defined above).

Preferred compounds for use in the present invention are azabicyclo derivatives (e.g. containing a bridged piperidyl group such as a tropyl, pseudotropyl, homotropyl or quinuclidinyl group) and benzoic acid derivatives (e.g. benzoates and benzamides) which act as antagonists of 5-HT at 5-HT 'M' receptors.

Particular mention may be made of the compounds which act as antagonists of 5-HT at 5-HT 'M' receptors disclosed in published British Patent Applications Nos. 2100259, 2125398, 2131420, 2132189 and 2145416 and published European Patent Applications Nos. 111608, 116255, 158265 and 94742.

A group of compounds described in UK Specification No. 2125398 may be represented by the general formula (II)

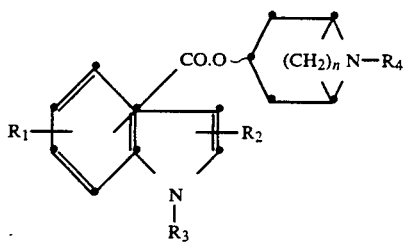

wherein
$R_1$ and $R_2$ independently represent hydrogen, halogen, $C_{1-4}$ alkoxy, hydroxy, amino, $C_{1-4}$ alkylamino, di($C_{1-4}$)alkylamino, mercapto or $C_{1-4}$ alkylthio;
$R_3$ represents hydrogen, $C_{1-4}$ alkyl, $C_{3-5}$ alkenyl, aryl or aralkyl;
$R_4$ represents hydrogen, $C_{1-7}$ alkyl, $C_{3-5}$ alkenyl or aralkyl;
n is 2 or 3;
the free valence is attached to either fused ring, and the azabicyclic ring is in either the exo or endo configuration, and acid addition salts and quaternary ammonium salts thereof.

In the compounds of formula (II) $R_1$ and $R_2$ may, for example, independently represent hydrogen, halogen or $C_{1-4}$ alkyl, $R_3$ may be, for example, hydrogen or $C_{1-4}$ alkyl and $R_4$ may be, for example, hydrogen, $C_{1-7}$ alkyl or aralkyl. The carbonyl group is preferably attached to the 3-position of the indole ring. The azabicyclic ring is preferably in the endo configuration.

Compounds described in UK Specifications Nos 2100259 and 2131420 may be represented by the general formula (III):

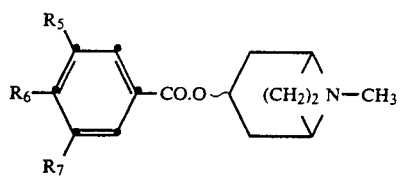

wherein
$R_5$ represents $C_{1-4}$ alkyl, $C_{1-4}$ alkoxy, or halogen; and
$R_6$ and $R_7$ independently represent hydrogen, $C_{1-4}$ alkyl, $C_{1-4}$ alkoxy or halogen;
provided that (a) when the azabicyclo ring is in the endo configuration and $R_7$ is hydrogen then $R_6$ is hydrogen or $R_5$ and $R_6$ are both alkyl, and (b) when the azabicyclic ring is in the exo configuration $R_5$ is a $C_{1-4}$ alkyl group; and pharmaceutically acceptable salts thereof.

Compounds of formula (III) in the endo configuration are preferred.

Compounds described in European Specification No 116255 may be represented by the general formula (IV)

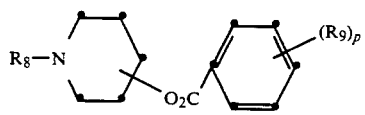

wherein
$R_8$ represents $C_{1-4}$ alkyl;
$R_9$ represents $C_{1-4}$ alkyl, $C_{1-4}$ alkoxy or halogen; and
p is zero or an integer from 1 to 5;
provided that when p is 2 the groups represented by $R_9$ can be the same or different and when p is 3, 4 or 5 the groups represented by $R_9$ are the same; and pharmaceutically acceptable salts thereof.

A group of compounds described in European Specification No. 94742 may be represented by the general formula (V):

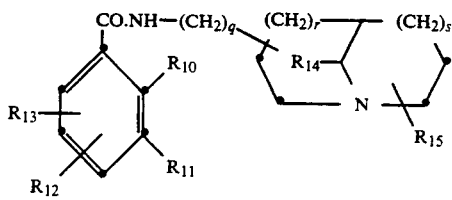

wherein
$R_{10}$ represents a $C_{1-6}$ alkoxy or amino N-substituted by one or two groups selected from $C_{1-6}$ alkyl or $C_{3-8}$ cycloalkyl or optionally N-substituted by $C_{4-5}$ polymethylene;
one of $R_{11}$, $R_{12}$ and $R_{13}$ is hydrogen and the other two are independently selected from hydrogen, chloro, bromo, trifluoromethyl, hydroxy, $C_{1-6}$ alkoxy, $C_{1-6}$ alkylthio, $C_{1-6}$ alkyl and amino;
one of $R_{14}$ and $R_{15}$ represents hydrogen, $C_{1-6}$ alkyl, phenyl or phenyl$C_{1-3}$alkyl, which phenyl moieties may be substituted by $C_{1-6}$ alkyl, $C_{1-6}$ alkoxy, $CF_3$ or halogen, and the other of $R_{14}$ and $R_{15}$ is hydrogen or $C_{1-6}$ alkyl;
q is zero or an integer from 1 to 4;
r is zero, or an integer from 1 to 3; and
s is zero, 1 or 2.

Preferred compounds of formula (V) are those wherein
$R_{10}$ is methoxy,
$R_{11}$ is hydrogen,
$R_{12}$ is 4-amino,
$R_{13}$ is 5-chloro (relative to the benzamide group),
$R_{14}$ and $R_{15}$ independently represent hydrogen or $C_{1-6}$ alkyl;
q is zero, r is 1 or 2 and s is zero, 1 or 2.

Preferred compounds for use according to the present invention are 1αH,3α,5αH-tropan-3-yl-3,5-dichlorobenzoate, also known as MDL 72222; 1αH, 3α,5αH-tropan-3-yl-3,5-dimethylbenzoate (MDL 72422); (3α-tropanyl)-1H-indole-3-carboxylic acid ester (ICS 205-930) and (±)-endo-4-amino-5-chloro-2-methoxy-N-(1-azabicyclo-[3.3.3]-non-4-yl)benzamide (BRL 24924).

The invention also provides a pharmaceutical composition which comprises at least one compound (e.g. an azabicyclo derivative or a benzoic acid derivative) which acts as an antagonist of 5-HT at 5-HT 'M' receptors, for the treatment of anxiety.

In a further aspect the invention provides the use of a compound (e.g. an azabicyclo derivative or a benzoic acid derivative) which acts as an antagonist of 5-HT at 5-HT 'M' receptors for the manufacture of a medicament for the treatment of anxiety.

Pharmaceutical compositions for use according to the present invention may be formulated in conventional manner, optionally with one or more physiologically acceptable carriers or excipients. For example, the compounds described in the aforementioned patent specifications may be formulated in the manner described therein.

Compounds for use according to the present invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of formula (I) and a suitable powder base such as lactose or starch.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The dose at which the compounds may be administered to man will depend upon the route of administration, the body weight of the patient and the potency of the compounds. For example, the compounds disclosed in the aforementioned patent specifications may be administered at doses in the ranges specified therein for the compounds, or at lower doses for example 0.5 µg to 20 mg e.g. 0.005–20 mg, preferably 0.05–10 mg per unit dose which may be administered, for example, 1 to 4 times per day.

Thus a unit dose of a compound of formula (II) as herein defined may contain from 0.2 to 250 mg of the active ingredient, and may be administered for example up to four times per day, such that the overall daily dose is in the range 0.5 to 500 mg.

A proposed dose of a compound of formula (III) is 0.5 mg to 100 mg e.g. 1 to 50 mg of the active ingredient per unit dose, which may be administered up to four times per day, to give a total daily dose in the range of 0.01 mg/kg to 10 mg/kg, e.g. 0.03 to 3.0 mg/kg.

A compound of formula (IV) may be administered in unit doses containing from 5 mg to 1000 mg e.g. 10 to 500 mg of the active ingredient, for example up to four times daily, such that the overall daily dose is in the range 0.1 mg/kg to 100 mg/kg e.g. 0.3 to 30 mg/kg.

The following example illustrates a pharmaceutical formulation containing (3α-tropanyl)-1H-indole-3-carboxylic acid ester for use in the treatment of anxiety.

Other compounds which are antagonists of 5-HT at 5-HT 'M' receptors may be formulated in a similar manner.

| Capsules | mg/capsule |
|---|---|
| Active Ingredient | 0.5 |
| *Starch 1500 | 98.5 |
| Magnesium Stearate BP | 1.0 |
| Fill Weight | 100.00 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

The anxiolytic activity of compounds for use according to the present invention has been demonstrated in the rat social interaction test.

RAT SOCIAL INTERACTION TEST

Social interaction in pairs of male rats is reduced by aversive stimuli such as unfamiliar territory and bright light. (Social interaction is active social contact e.g. sniffing, following, crawling under and over, boxing and fighting). Reduced social interaction can be prevented by anxiolytic agents. Thus, the anxiolytic activity of a compound can be evaluated by measuring its effect on the behaviour of rats subject to such aversive conditions.

The test procedure used was based on that described by S. File (J. Neuroscience Methods, Vol. 2, 219–238, 1980; and Recent Advances in Neuropsychopharmacology, Vol. 31, 241–251, 1981).

TEST COMPOUNDS (A) (3α-tropanyl)-1H-indole-3-carboxylic acid ester
(B) 1αH, 3α, 5αH-tropan-3-yl-3,5-dichlorobenzoate

TEST PROCEDURE

Male Hooded Lister rats (100–140 g) were kept in cages of 5 under low light for at least 4 days before testing. Individual rats were then taken from cages distant from each other and the test compounds administered orally (as a suspension in 5% acacia solution).

Control animals received acacia solution.

Diazepam was administered to some animals in place of the test compound, as a standard.

Following dosing, the animals were placed in individual cages for 1 hour. They were then moved to an enclosed test arena (61×61×41 cm high) illuminated by two overhead strip lights to provide a high light intensity. The rats were observed and the amount of time that the pairs of rats spent in active social contact was recorded with a stop-watch over a 10 minute test period. Their behaviour was also monitored and recorded via a camera above the test arena. Locomotor activity of the rats was measured automatically by recording the number of light beam crossings which occurred in the 10 minute test period.

RESULTS

Diazepam

Minimum effective dose: 500 µg/kg (Oral).

| Test Compound | Dose range tested (µg/kg) oral | Minimum effective Dose* (µg/kg) oral |
|---|---|---|
| A | 0.01–100 | 0.01 |
| B | 1–100 | 10 |

*The minimum effective dose of the test compound is the dose required to produce a significant increase in social interaction as compared with the control animals (p = <0.05).

At doses of 4 mg/kg (orally) and above the effect of diazepam on social interaction is masked by sedation, as indicated by a reduction in locomotor activity.

The test compounds produced no reduction in locomotor activity or any other adverse effect up to the highest doses tested, i.e. 100 µg/kg.

I claim:

1. A method for the treatment of anxiety in a human or animal subject suffering from or susceptible to anxiety which comprises administering to the human or animal subject an effective amount for the treatment of anxiety in said subject of an azabicyclo derivative which acts as an antagonist of 5-hydroxytryptamine (5-HT) at 5-HT "M" receptors, wherein said azabicyclo derivative is a conjugate formed from an indole derivative connected by an amide group to a tropyl group; or a physiologically acceptable salt or solvate thereof.

2. A method according to claim 1 wherein said azabicyclo derivative or a physiologically acceptable salt or solvate thereof is administered in a dose of 0.5 µg to 20 mg from 1 to 4 times per day.

3. A method according to claim 2 wherein the dose is from 0.05 mg to 10 mg from 1 to 4 times per day.

4. A method according to claim 1 wherein said azabicyclo derivative is administered orally, buccally, parenterally, rectally or as a depot preparation.

5. A method according to claim 1 wherein said azabicyclo derivative is administered orally.

* * * * *